United States Patent [19]

Young

[11] Patent Number: 4,558,598

[45] Date of Patent: Dec. 17, 1985

[54] ULTRASONIC LINEAR ARRAY WATER NOZZLE AND METHOD

[75] Inventor: Fred D. Young, Bellevue, Wash.

[73] Assignee: The Boeing Company, Seattle, Wash.

[21] Appl. No.: 618,227

[22] Filed: Jun. 7, 1984

[51] Int. Cl.[4] .......................................... G01N 29/04
[52] U.S. Cl. .................................................... 73/644
[58] Field of Search ........................ 73/644, 641, 636; 239/4

[56] References Cited

U.S. PATENT DOCUMENTS

| | | | |
|---|---|---|---|
| 2,751,783 | 6/1956 | Erdman | 73/634 |
| 3,255,626 | 6/1966 | Van Der Veer | 73/644 |
| 3,303,691 | 2/1967 | Beaujard et al. | 73/644 |
| 3,373,437 | 3/1968 | Sweet et al. | 239/4 |
| 3,420,097 | 1/1969 | Battermann et al. | 73/644 |
| 3,485,088 | 12/1969 | O'Connor | 73/629 |
| 3,501,947 | 3/1970 | Hetherington | 73/640 |
| 3,625,051 | 12/1981 | Uozumi | 73/634 |
| 3,662,590 | 5/1972 | Shiraiwa et al. | 73/644 |
| 3,741,003 | 6/1973 | Gunkel | 73/637 |
| 3,745,833 | 7/1973 | Armstrong | 73/628 |
| 3,908,445 | 9/1975 | Verdon et al. | 73/644 |
| 3,910,104 | 10/1975 | Davies | 73/641 |
| 3,946,599 | 3/1976 | Patt | 73/644 |
| 4,033,178 | 7/1977 | Holt et al. | 73/644 |
| 4,164,150 | 8/1979 | Ries et al. | 73/644 |
| 4,167,880 | 9/1979 | George | 73/644 |
| 4,388,343 | 6/1983 | Voss et al. | 239/4 |
| 4,403,510 | 9/1983 | deWalle et al. | 73/644 |

FOREIGN PATENT DOCUMENTS 255105 2/1963 Australia .
1275693 10/1961 France .

Primary Examiner—Anthony V. Ciarlante
Attorney, Agent, or Firm—Eugene O. Heberer; Delbert J. Barnard

[57] ABSTRACT

An ultrasonic linear array water nozzle (10, 10A) wherein water is coupled with ultrasonic energy between linear array transducers (126) and a workpiece (132) under inspection. The nozzle includes a water receiving plenum chamber (22) extending for the length of the nozzle and for the length of linear array transducers. Plenum chamber (22) supplies water immediately downstream of the transducers where water is coupled with ultrasonic energy from the transducers. The nozzle has a main body (88) downstream of the transducers and has downstream water paths in the form of waveguides (190) which are spaced by air gaps (186), the waveguides each extending downstream in the shape of an exponential horn. The waveguides (190), formed by consecutive plates (168) having air gaps (186), are each in respective alignment with an individual transducer (126).

28 Claims, 6 Drawing Figures

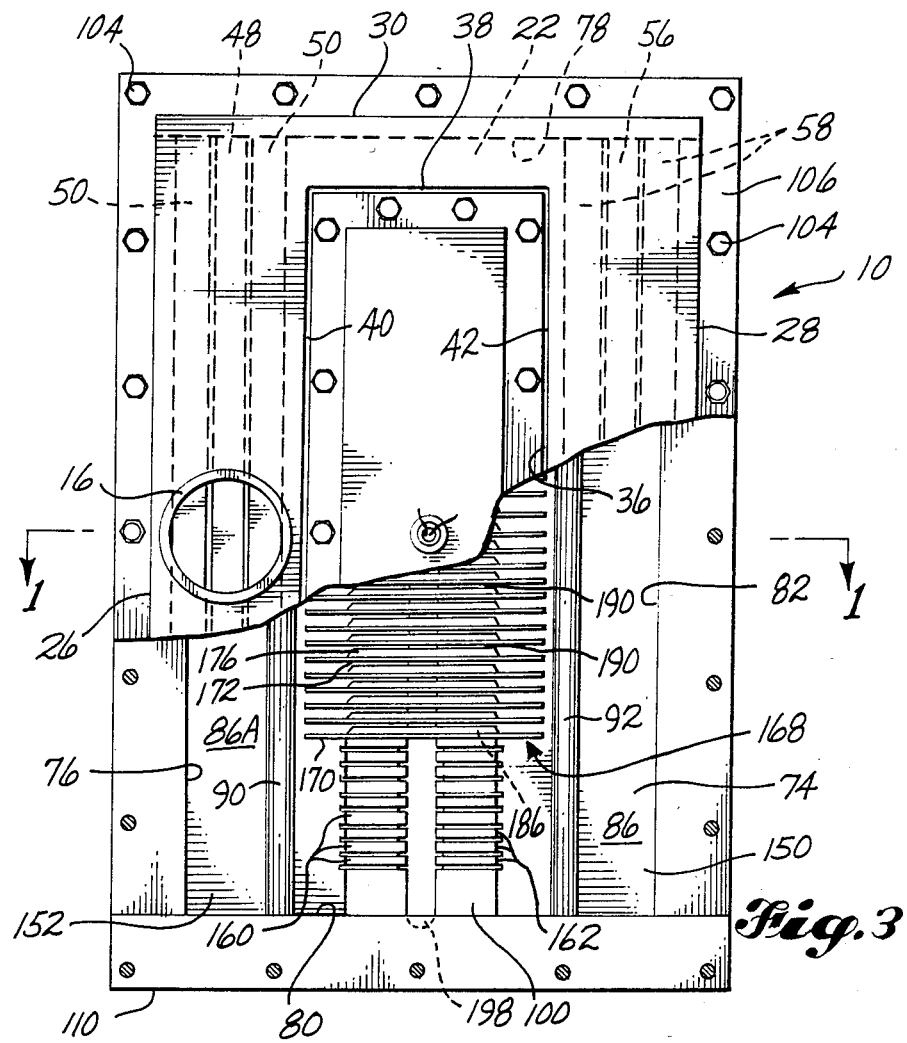

ULTRASONIC LINEAR ARRAY WATER NOZZLE AND METHOD

DESCRIPTION

TECHNICAL FIELD

The invention relates to a nozzle for ultrasonic testing of materials in which water is coupled to ultrasonic energy and a method for employing the nozzle.

BACKGROUND ART

The ultrasonic inspection of materials for detection of defects is well-known. Scanners using linear array transducers have normally been used in an immersion tank with the linear array transducer submerged in water. Such systems have normally been operated in the pulse-echo mode which requires only an array transducer.

Laminated structures such as those including honeycomb are highly attenuating and thus require higher ultrasonic energy to inspect the parts, particularly for separated lamination areas. This makes through-transmission inspection a more practical method. To build a scanner for through-transmission inspection for immersion inspection would be impractical because a large complex scanning mechanism and tank would have to be built to accommodate large composite laminated structures now being fabricated. In addition, honeycomb structures tend to float and this provides an additional handling problem.

Conventional scanners were generally made to scan in both the X and Y directions, the scanning being along a line in each direction.

A search of the patent literature discloses apparatus and methods which propose solutions for ultrasonic inspections. For example, U.S. Pat. No. 2,751,783 to Erdman discloses a stream of liquid coupling medium employed in a direct line and forming an uninterrupted liquid bridge between an ultrasonic transducer and a test object, the stream carrying consecutively both the transmitted and reflected signals.

U.S. Pat. No. 3,745,833 to Armstrong discloses a thickness gauge for determining the position of a surface of a workpiece. The device has a housing shaped to constrain water to flow coaxially into the upper end of a tube 15, FIG. 3, which is spaced slightly from the inner surface of the housing, and water flows downwardly through a flow alignment member in the tube, the member comprising a cylindrical block 19 having a number of axially extending cylindrical bores 20. Laminar flow is developed in the tube 15 and the cylindrical bores 20.

U.S. Pat. No. 3,908,445 to Verdon et al provides an ultrasonic transducer in a sleeve with flow straightening means downstream of the transducer for producing substantial laminar flow of water at the outlet of the sleeve. The flow straightening means comprises a bundle of tubes which fill the sleeve section. In order to maintain a positive water flow pressure within the outlet end of the sleeve, and thereby prevent cavitation, the outlet end is provided with a flow restrictor shaped to disturb laminar flow conditions as little as possible.

U.S. Pat. No. 3,910,104 to Davies provides an array of ultrasonic transducers, the length of the array of transducers being greater than the width of a plate being tested.

The following additional patents found in the search disclose nozzle constructions of general interest:
U.S. Pat. No. 3,255,626, W. R. Van Der Veer
U.S. Pat. No. 3,303,691, L. Beaujard et al
U.S. Pat. No. 3,420,097, J. Battermann et al
U.S. Pat. No. 3,485,088, D. T. O'Connor
U.S. Pat. No. 3,501,947, M. J. Hetherington
U.S. Pat. No. 3,625,051, Sutekiyo Uozumi
U.S. Pat. No. 3,662,590, Shiraiwa et al
U.S. Pat. No. 3,741,003, W. A. Gunkel
U.S. Pat. No. 3,946,599, J. Patt
U.S. Pat. No. 4,033,178, Holt et al
U.S. Pat. No. 4,164,150, Ries et al
U.S. Pat. No. 4,167,880, L. W. George
U.S. Pat. No. 4,403,510, deWalle et al
Australia No. 255,105, Taylor
French No. 1,275,693, U.K. Atomic Energy Authority

DISCLOSURE OF THE INVENTION

The invention is an ultrasonic linear array water nozzle and method wherein water is coupled with ultrasonic energy between linear array transducers and a workpiece under inspection. A transmitting nozzle is positioned on one side of a workpiece and a receiving nozzle equivalent to the transmitting nozzle is positioned on the other side of the workpiece.

The nozzles include linear array ultrasonic transducers, a water receiving plenum chamber upstream within the nozzle. The plenum chamber extends substantially for the length of the nozzle and the length of the linear array of transducers. The plenum chamber is formed to supply water immediately downstream of the transducers to couple ultrasonic energy from the transducers with the water.

The nozzle has a main body downstream of the transducers and forms a downstream water path from adjacent the transducers to a downstream discharge end of the nozzle. The main body has a linear length extending at least to the extent of the linear array of the transducers. The main body closely downstream of the transducers has an upstream opening transversely as great as the transducers, the upstream opening extending along the linear array of transducers. The upstream opening forms a part of the downstream water path which narrows transversely to the discharge end to form a narrow discharge opening, substantialy narrower transversely than the transducers and the upstream opening. The discharge opening extends for the linear length of the linear array of transducers.

Waveguides extend from the upstream opening in the main body to the narrow discharge end and each waveguide forms a separate part of the water path from the upstream opening to the discharge end. Each waveguide is rectangular in cross section and is transversely in the shape of an exponential horn. Each waveguide is aligned with a respective transducer to receive the ultrasonic energy therefrom and each waveguide is closed from the upstream opening to the discharge end.

The waveguides are juxtaposed having two spaced walls transverse to the linear length to the transducers array. There is an air gap along the surface of each transverse wall forming the waveguides, the air gap extending transversely to the extent of the waveguide. The air gaps prevent transfer of ultrasonic energy or "crosstalk" in the linear length direction from one juxtaposed waveguide to another.

The plenum chamber has baffles extending in the linear length to direct water received in the plenum chamber into the nozzle to the extent of its length and around the transducers to the extent of the linear length. Dams extend in the linear length direction internally for the length of the nozzle, downstream of the baffles, transversely on opposite sides of the transducers to reduce turbulence of the water flow around and below the transducers and into the waveguides to aid in achieving laminar flow in the waveguides. The dams are in a second chamber below the plenum chamber. They are spaced between the transducers and outer opposite transversely spaced walls of the second chamber.

According to the invention, a method of testing a workpiece for structural irregularities with water coupled with ultrasonic energy includes introducing water under pressure into a plenum chamber of an ultrasonic linear array water nozzle, flowing the water downstream in the nozzle around and downstream of the linear array ultrasonic transducers, coupling the water with ultrasonic energy from the linear array ultrasonic transducers, flowing the water coupled with energy from adjacent the transducers into laminar flow paths, spaced along the linear array transducers. The flow paths are narrowed downstream transversely to the linear array to form narrow downstream discharge outlets. The water coupled with energy is discharged from the narrow outlets onto a workpiece being tested. The nozzle is moved along the workpiece transversely to the linear array on a workpiece path for the length of the test area and then the nozzle is moved in the linear direction to an adjacent workpiece path to again move the nozzle transversely to the linear array for the length of the test area. The movement is continuous on the workpiece according to the transverse and linear movements until a predetermined area of the workpiece is tested.

During the testing one nozzle is positioned on one side of the workpiece to discharge water coupled with ultrasonic energy onto the workpiece in a predetermined area and a second equivalent nozzle is positioned on the other side of the workpiece to discharge water coupled with ultrasonic energy onto the workpiece in the predetermined area opposite the area on the one side. One of the nozzles is a transmitting nozzle and the other nozzle is a receiving nozzle.

It has been determined that the preferred maximum distance of the water path between the narrow or small discharge outlets and the workpiece is about four inches. However to achieve higher sensitivity, the receiving linear array water nozzle path distance would be about one inch from the part surface.

The linear array transducers can cover a three or four inch wide path, depending upon the number of transducer elements, in contrast to a quarter inch wide path for the conventional water jets which scan in a line in the X and Y directions rather than in paths juxtaposed to each other along the surfaces of the workpiece.

The invention as made includes a 32 element linear array transducer. As stated the waveguides eliminate the transfer of ultrasonic energy into adjacent waveguides by means of the air gaps. The waveguides also enhance laminar flow.

Tests have shown that laminar water flow can be obtained up to four inches of water path and water paths greater than four inches distort the ultrasonic signal and further reduce sensitivity. Maximum sensitivity in the through-transmission mode is obtained when the receiver water path distance is less than one inch from the workpiece. The exponential horn configuration provides increased laminar flow and amplifies the signals.

Nozzles, according to the invention, have provided a great sensitivity in the through-transmission mode where the workpieces were laminated plates, including honeycomb structures, and provided excellent readings indicating delamination between laminated plates in the workpiece. That is, where delamination has occurred, the lack of signals and the energy moving therethrough indicates the defect.

Further advantages of the invention may be brought out in the following part of the specification wherein small details have been described for the competence of the disclosure, without intending to limit the scope of the invention which is set forth in the appended claims.

BRIEF DESCRIPTION OF THE DRAWINGS

Referring to the accompanying drawings which are for illustrative purposes:

FIG. 3 is a partially broken away plan view of the invention looking down on FIG. 1;

FIG. 4 is a view of the linear array of the transducers and illustrating the positioning of waveguides below respective transducers, the waveguides extending from just below the transducers to the small discharge end of the nozzle;

BEST MODE FOR CARRYING OUT THE INVENTION

Figure 1:
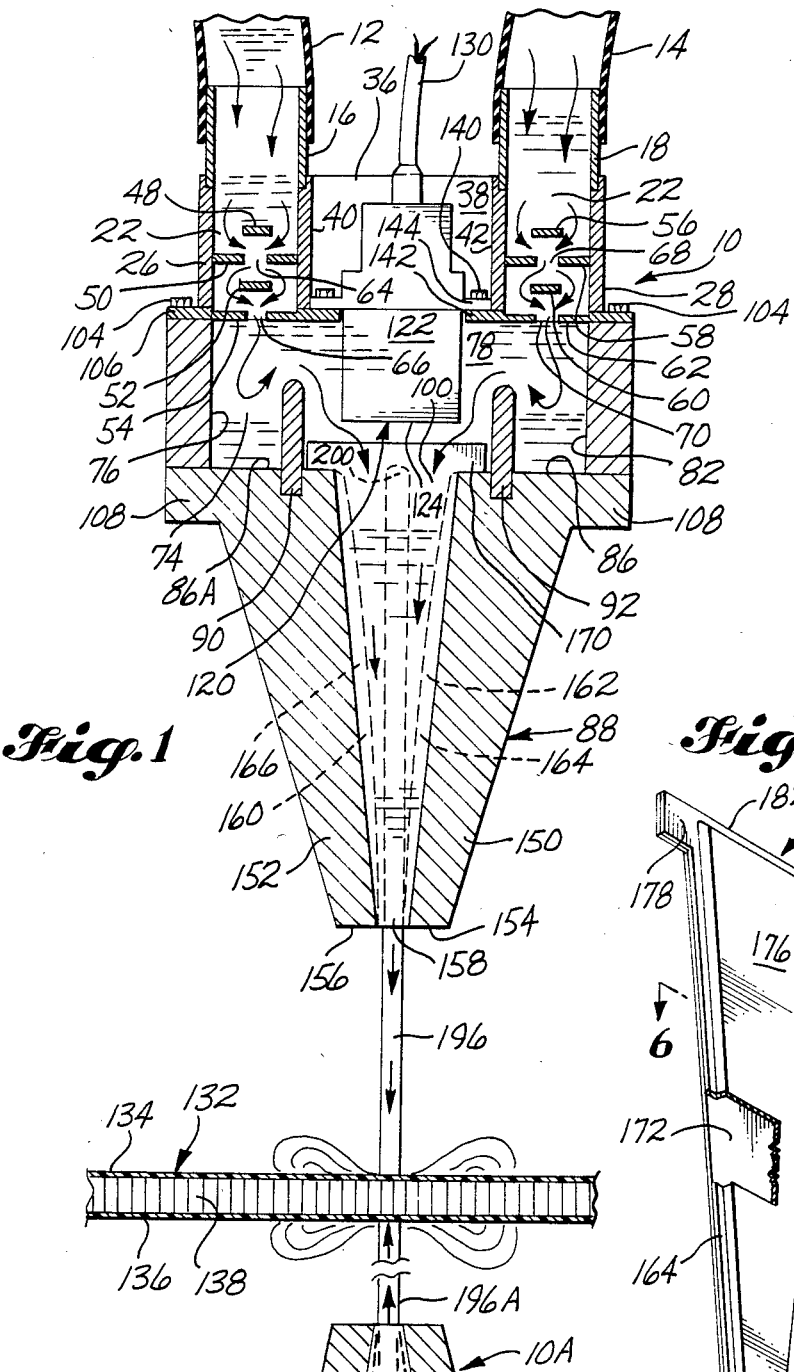
FIG. 1 is a cross-sectional transverse view of an ultrasonic linear array water nozzle, according to the invention, taken along the lines 1—1 in FIG. 3, and including a workpiece and a fragmentary view of an identical nozzle on the other side of the workpiece for through-transmission testing.
Figure 5:
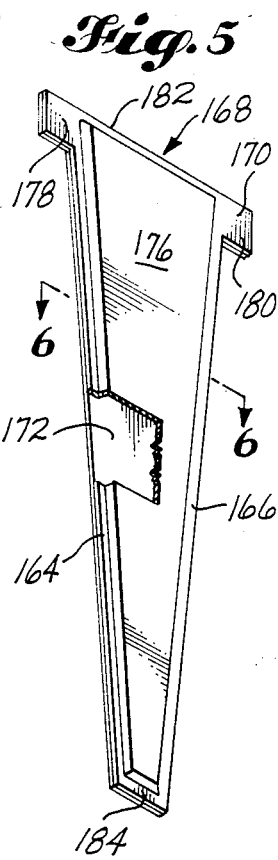
FIG. 5 is a pictorial view of one wall for forming a waveguide.
Figure 6:
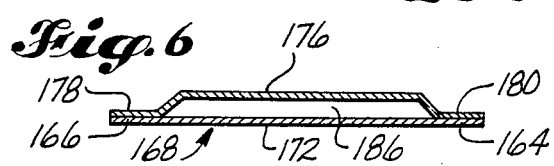
FIG. 6 is a cross-sectional view taken along the lines 6—6 in FIG. 5.
Figure 2:
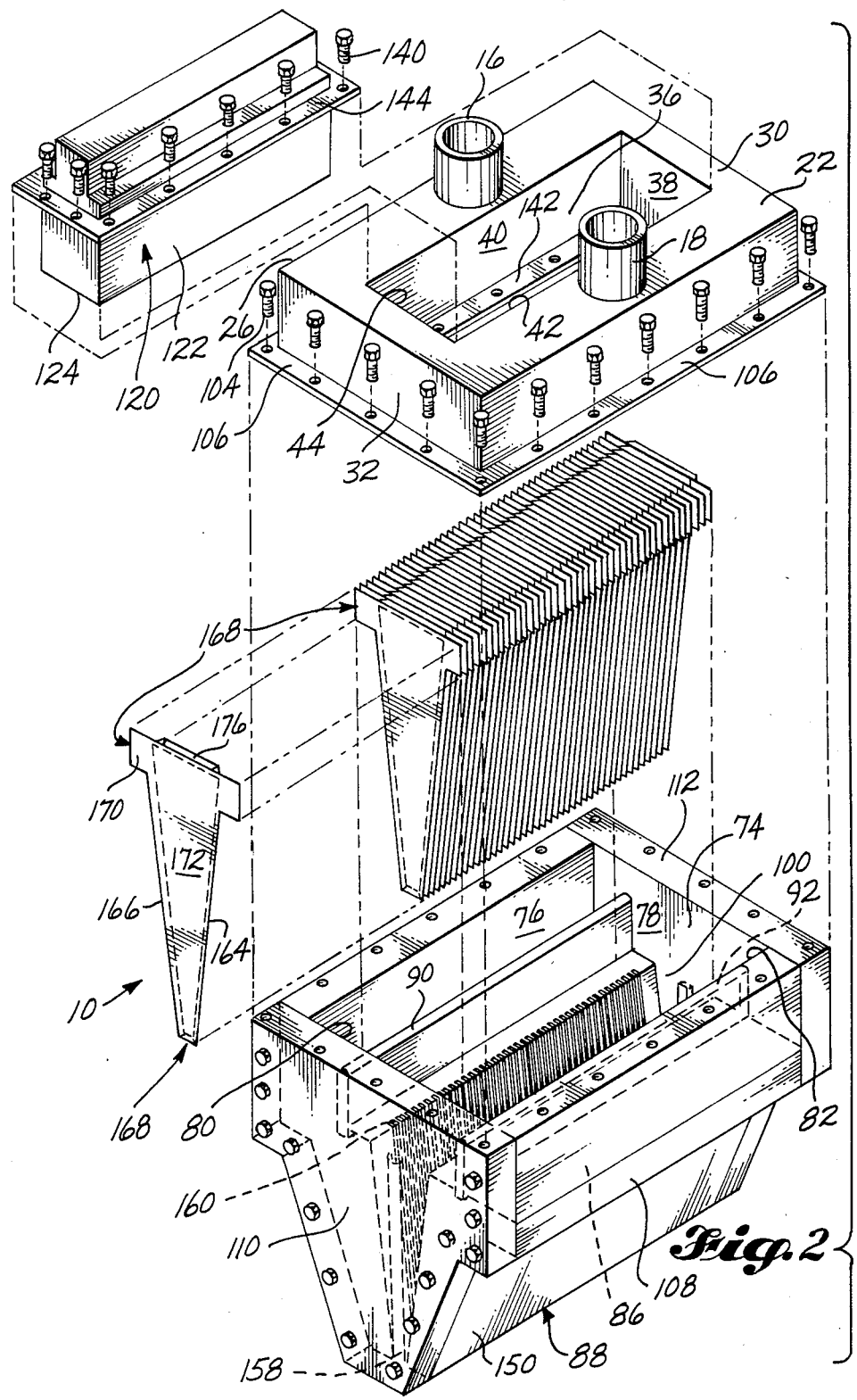
FIG. 2 is an exploded view of the nozzle shown in FIG. 1.

Referring again to the drawings, there is shown in FIGS. 1-3 an ultrasonic linear array water nozle, generally designated as 10. Upstream of the nozzle are water supply connections 12 and 14 for supplying water under pressure at about 40 pounds per square inch, and connected to cylindrical water inlets 16 and 18, each of which supplies water to a rectangular plenum chamber 22 having four outer walls 26, 28, 30, and 32. The chamber 22 has an open rectangular central portion 36, formed by four walls 38, 40, 42, and 44. Thus, in the plenum chamber 22 there is a rectangular flow path surrounding the walls 38, 40, 42 and 44.

Extending in a linear direction downstream of the inlets 16 and 18 and outwardly of the walls 40 and 42, respectively, are horizontal baffle plates 48, 50, 52, 54, 56, 58, 60 and 62, extending for the full linear length of the plenum chamber to cause the incoming water to flow for the full length of the chamber and into the rectangular path formed around the inner walls. The incoming water moves horizontally, as may be imagined from the positions of the baffles, as shown in FIG. 3, and moves downstream as shown by the arrows in FIG. 1 through openings 64, 66, 68 and 70 in the baffles 50, 54, 58 and 62, respectively. The openings 64, 66, and 58, 70 extend for the full length of the plenum chamber and permit the water to flow downstream into a second generally rectangular chamber 74. The chamber 74 has outer walls 76, 78, 80 and 82 and has a bottom walls 86, 86A forming tops of nozzle main body portion 88. Fitted into the walls 86, 86A are elongated members 90 and 92 extending upwardly into the chamber 74 and forming dams. The dams 90, 92 serve to reduce turbulence in the water flow from the plenum chamber 22, as indicated by the arrows in FIG. 1, as the water flows downstream to the chamber 74 on both sides of the dams, extending for the full length of the chamber, and then over the dams into a wide opening 100 centrally positioned in the walls 86, 86A and extending for the linear length of the nozzle.

The plenum chamber 22 and the walls of the chamber 74 are secured to the main body 88 by means of bolts 104 through flanges 106 at the external bottom of the plenum chamber and flanges 108 forming the periphery of the upper surface of the walls 86, 86A FIG. 1. At the linear end of the main body portion there are end plates 110 and 112, FIGS. 2 and 4, extending transversely with respect to the nozzle and are secured to transverse portions of the flange 106 by the bolts 104.

Positioned within the rectangular opening 36 within the walls 38, 40, 42 and 44 of the plenum chamber 22 and extending downwardly into the chamber 74 are linear array transducers, generally designated as 120. The transducers are formed in a generally rectangular ceramic block 122 which has multiple saw cuts 123 into its lower surface 124 to form a multiple number of transducer elements 126, FIG. 4, to form the linear array of transducers in a PZT electrical crystal in the block 122. The cuts 123 extend transversely and each transducer 126 similarly extends transversely between a pair of cuts. The number of transducers, for example, may be 32 so that the transducers could be described as a 32 element linear array transducer.

The transducers are conventionally connected to a three or four hundred volt pulse generator by electrical connections 130. The pulse generator, its amplifier, and readout device are not shown. The transducer assembly can be used as a transmitter or receiver and in the structure shown the nozzle 10 has transmitting transducers and the nozzle 10A, shown fragmentarily in FIG. 1 would have receiving transducers, the structures in 10A, being identical to the structures in nozzle 10. The readout device would be connected to the receiving transducers and which would receive the signals indicating delaminations in a laminated test plate as shown by the plate 132 in FIG. 1. Here, the plate has a series of upper and lower laminations 134 and 136 with a honeycomb structure 138 therebetween.

The transducer 120 is secured to flanges 142 by bolts 140 extending through the transducer flange 144.

In the main body 88, inwardly of the transverse end plates 110 and 112 are two linearly directed side plates 150 and 152, spaced from each other at their upstream ends by the wide opening 100 and spaced at downstream discharged ends 154 and 156 by narrow discharge opening 158. The space between opening 100 and discharge outlet 158 is tapered in cross section, FIG. 1, and is in the shape of an exponential horn. The inner walls of the members 150, 152 have aligned spaced respective grooves 160 and 162 adapted to receive edges 164 and 166 of waveguide forming plates 168, FIGS. 1-6. The plates 168 have a T-bar 170 at their upstream ends and downstream thereof have a central narrowing plate portion 172 in the shape of an exponential horn. Opposite the plate portion 172 is a second plate 176 which is bent adjacent the edges 164 and 166 toward the plate 172 and its edges 178 and 180 are secured to edges 166, 164 respectively. Upstream edges 182 and downstream edge 184 are also secured to the plate portion 172 to form an enclosed air gap 186 for the substatial length and breadth of the plate 172. The edges 164 and 166 fit into the grooves 162 and 160, respectively in the members 150 and 152. When so fitted the upstream edges 178, 166, and 180, 164 rest on wall surfaces 86 and 86A, respectively, within the chamber 74, FIG. 1.

As best seen in FIG. 3, when the waveguide forming members 168 are in the grooves 160 and 162 waveguides 190 of exponential shape are formed by the surface of a plate 172 opposite the surface of an adjacent plate 176. Shown in FIGS. 1 and 4, the downstream ends of the transducers 126 are adjacent the upstream ends of the plates 168 and as indicated in FIG. 4, the transducers are in alignment with the waveguides formed by the plates 168 fitted into the grooves 160 and 162. As may be noted in FIG. 4 the grooves 160 extend linearly beyond the transducers to aid in maintaining the laminar flow formed in the waveguides which receive the water coupled with the ultrasonic energy to be discharged on a plate as 124 in a laminar flow stream 196, FIG. 1. To aid in maintaining the laminar flow through the exponential horn area, grooves 198 and 200 are formed in end plates 110 and 112, respectively. These semicircular grooves, extending downstream from the upper ends of the plates adjacent the surfaces 86 and 86A, aid in maintaining a laminar flow throughout the waveguides and in the discharged stream 196.

On the other side of the test plate 124, from a transmitting nozzle 10, is an identical nozzle 10A for receiving the signals indicating defects in the plate being tested. In operation, as indicated, the water is introduced into the plenum chambers of both nozzles 10 and 10A and moved through the baffles and over the dams 90 and 92 to a flow path below the transducers where water is coupled with ultrasonic energy along the linear array transducers and continued to flow into the waveguides from the large opening 100 out of the small openings 158 where the waveguides terminate. The nozzles are moved relative to the plate 132 transversely together in one direction to inject water onto paths on the plate equal to the length of the nozzles in the linear direction. Defects in the plates such as an area of delamination is reflected into the readout of the receiving transducers. At the end of one run or the length of the plate 132, the plate and nozzles are moved relative to each other so that a run may be made along a path adjacent the path just completed, and such runs are made continuously until the entire plate has been tested.

The exponential horn shape of the waveguides provides a laminar flow structure and amplifies signals received relative to defects in the material being tested. The air gaps in the waveguides reduces "crosstalk" between the waveguides; that is, air gaps tend to eliminate the transfer of ultrasonic energy into adjacent waveguides. Visual observation shows that water nozzles, according to the invention, with the present waveguides provide a very stable and uniform flow of water in contrast to prior art nozzles.

The estimated maximum water path distance, that is, the length of the water stream 196, should be about four inches. However, to achieve the highest sensitivity, the receiving linear array nozzle water path should be approximately no greater than one inch from the surface of the part being tested. The linear length of nozzles according to the invention are generally three or four inches.

The invention and its attendant advantages will be understood from the foregoing description and it will be apparent that various changes may be made in the form, construction, and the arrangements of the parts of the invention without departing from the spirit and scope thereof or sacrificing its material advantages, the arrangements hereinbefore described being merely by way of example. I do not wish to be restricted to the specific forms shown or uses mentioned except as defined in the accompanying claims.

What is claimed is:

1. An ultrasonic linear array water nozzle in which water is employed to couple ultrasonic energy between linear array transducers and a workpiece under inspection, comprising:
   linear array ultrasonic transducers in said nozzle;
   an upstream plenum chamber for receiving water upstream within said nozzle and associated with said transducers to distribute water along the length of the nozzle and the linear length of the array of transducers;
   a water path in said nozzle from said plenum chamber and immediately downstream of said transducers so ultrasonic energy from the transducers is coupled with the water;
   a main body in the nozzle downstream of the transducers and forming a downstream water path from the transducers to a discharge end of the nozzle;
   said main body in the nozzle having a linear length extending at least the extent of the linear array of the transducers;
   said main body downstream of the transducers having a wide opening adjacent the transducers, transverse to the linear length, and the opening forming a part of the downstream water path, and the water path narrowing transversely toward the discharge end to a narrow discharge opening, the discharge opening being substantially narrower transversely than the transducers and the wide opening, and extending along the linear length; and
   waveguides extending in the main body from the wide opening adjacent the transducers to the narrow discharge end;
   each waveguide being aligned with a respective transducer to receive the ultrasonic energy therefrom and each waveguide forming a part of the water path from the transducers to the discharge end.

2. The invention according to claim 1 in which:
   the main body from the wide opening to the narrow discharge end being transversely in the shape of an exponential horn.

3. The invention according to claim 1 in which:
   each waveguide has two spaced walls extending transversely to the linear length;
   the spaced transverse walls terminating in opposite closing end walls, the closing end walls being tapered from adjacent the wide opening to the narrow discharge opening, each waveguide being generally rectangular in cross section.

4. The invention according to claim 1 in which:
   the waveguides being juxtaposed and each having two spaced walls transverse to the linear length;
   the spaced transverse walls terminating in opposing closing end walls, the closing end walls being tapered from adjacent the wide opening to the narrow discharge opening, each waveguide being generally rectangular in cross section;
   the waveguides having means to prevent transfer of the ultrasonic energy in the linear length direction from one juxtaposed waveguide to another.

5. The invention according to claim 4 in which:
   said means to prevent transfer of ultrasonic energy between the waveguides is an air gap formed along a surface of the transverse walls and extending to terminate in the opposing closing end walls.

6. The invention according to claim 4 in which:
   said plenum chamber has water inlets upstream of the transducers and on opposite sides thereof;
   baffles in said plenum chamber on opposite sides of said transducers, the baffles extending in the linear length to the extent of the nozzle length to direct water in the plenum chamber in the nozzle to the extent of its length and around the transducers to the extent of the linear length.

7. The invention according to claim 6 including:
   a dam spaced transversely from each side of the transducers and downstream of the baffles to reduce turbulence of the water flow around and downstream of the transducers and into the waveguides to achieve laminar flow.

8. The invention according to claim 7 in which:
   said means to prevent transfer of ultrasonic energy between the waveguides is an air gap formed along a surface of the transverse walls and extending to terminate in the opposing closing end walls.

9. The invention according to claim 1 in which:
   said plenum chamber has baffles extending in the linear length to direct the water received in the plenum chamber in the nozzle to the extent of its length and around the transducers to the extent of the linear length.

10. The invention according to claim 9 including:
    a dam extending in the linear length on each side of the transducers and downstream of the baffles to reduce turbulence of the water flow around and below the transducers and into the waveguides to aid in achieving laminar flow in the waveguides;
    the dams being in a second chamber downstream of the plenum, the dams being spaced between the transducers and outer opposite transversely spaced walls of the second chamber.

11. The invention according to claim 10 in which:
    said plenum chamber has water inlets upstream of the transducers and on opposite sides thereof;
    said baffles being positioned on opposite sides of said transducers downstream of the inlets.

12. An ultrasonic linear array water nozzle wherein water is coupled with ultrasonic energy between linear array transducers and a workpiece under inspection, comprising:
    linear array ultrasonic transducers in said nozzle;
    a water receiving plenum chamber upstream within said nozzle;
    said plenum chamber extending substantially for the length of the nozzle and the length of the linear array of transducers;
    said plenum chamber being formed to supply water immediately downstream of said transducers to couple ultrasonic energy from the transducers with the water;

a main body of the nozzle downstream of the transducers and forming a downstream water path from adjacent the transducers to a downstream discharge end of the nozzle;

said main body having a linear length extending at least to the extent of the linear array of the transducers;

said main body closely downstream of the transducers having an upstream opening transversely as great as the transducers, said upstream opening extending along the linear array of transducers;

said upstream opening forming a part of said downstream water path, said downstream water path narrowing transversely to said discharge end to form a narrow discharge opening substantially narrower transversely than the transducers and the upstream opening, said discharge opening extending for the length of the linear array of transducers; and waveguides extending from the upstream opening in the main body to the narrow discharge end, and each waveguide forming a separate part of the water path from the upstream opening to the discharge end, each waveguide being rectangular in cross section and being transversely in the shape of an exponential horn;

each waveguide being aligned with a respective transducer to receive the ultrasonic energy therefrom, each waveguide being closed from the upstream opening to the discharge end.

13. The invention according to claim 12 in which:

the waveguides are juxtaposed, having two spaced walls transverse to the linear length; and means in the waveguides to prevent transfer of ultrasonic energy in the linear length direction from one juxtaposed waveguide to another.

14. The invention according to claim 13 in which:

said means to prevent transfer of ultrasonic energy in the linear length direction between waveguides is an air gap formed along a surface of the transverse walls, the air gap extending transversely to the extent of the waveguides.

15. The invention according to claim 14 in which:

said plenum chamber has baffles extending in the linear length to direct the water received in the plenum chamber in the nozzle to the extent of its length and around the transducers to the extent of the linear length.

16. The invention according to claim 15 including:

dams extending in the linear length direction internally for the length of the nozzle, transversely on opposite sides of the transducers, and downstream of the baffles to reduce turbulence of the water flow around and below the transducers and into the waveguides to aid in achieving laminar flow in the waveguides;

the dams being in a second chamber below the plenum, the dams being spaced between the transducers and outer opposite transversely spaced walls of the second chamber.

17. The invention according to claim 16 in which:

said plenum chamber has water inlets upstream of the transducers and on opposite sides thereof;

said baffles being positioned on opposite sides of said transducers downstream of the inlets.

18. The invention according to claim 17 in which:

one of said nozzles is positioned on one side of said workpiece to discharge water coupled with ultrasonic energy onto said workpiece in a predetermined area;

another of said nozzles is positioned on the other side of said workpiece to discharge water coupled with ultrasonic energy onto said workpiece in a predetermined area opposite said area on the one side.

19. A method of testing a workpiece for structural irregularities with water coupled with ultrasonic energy, comprising:

introducing water under pressure into a plenum chamber of an ultrasonic linear array water nozzle;

flowing said water downstream in said nozzle around and downstream of linear array ultrasonic transducers;

coupling said water with ultrasonic energy from said linear array ultrasonic transducers;

flowing said water coupled with said energy from adjacent said transducers into laminar flow paths, said flow paths being spaced along the linear array transducers and narrowing downstream transversely from the linear array to form narrow downstream discharge outlets;

flowing said coupled water from said discharge outlets onto a workpiece being tested; and moving said nozzle along said workpiece transversely to the linear array on a workpiece path for the length of the test area and then moving the nozzle in the linear direction to an adjacent workpiece path to again move the nozzle transversely to the linear array for the length of the test area, and continuously moving the nozzle on the workpiece according to the said transverse and linear movements until a predetermined area of the workpiece is tested.

20. The method according to claim 19 including:

flowing said coupled water into laminar flow paths, each path being in the shape transversely of an exponential horn.

21. The method according to claim 19 including:

flowing said coupled water into laminar flow paths, each path forming a waveguide extending from adjacent a respective transducer to a discharge outlet.

22. The method according to claim 21 including:

flowing said coupled water into said waveguides and preventing transfer of ultrasonic energy between waveguides in the direction of the linear array transducers.

23. The method according to claim 21 including:

flowing said coupled water into said waveguides and preventing transfer of ultrasonic energy between waveguides in the direction of the linear array transducers, preventing said energy transfer between said waveguides by means of air gaps therebetween.

24. The method according to claim 21 including:

flowing said coupled water into laminar flow paths forming said waveguides in which said waveguides are rectangular in cross section.

25. The method according to claim 19 including:

introducing water into the plenum chamber into two inlets upstream of the transducers, the inlets being on opposite sides of the transducers.

26. The method according to claim 25 including:

flowing the water into the plenum chamber on opposite sides of the transducers and through baffles extending in the linear array length and directing water in the plenum chamber to the extent of the plenum chamber, and linear array length.

27. The method according to claim 26 including:
flowing said water downstream of said baffles into a second chamber around the transducers; and
flowing the water in the second chamber over dams on both sides of the transducers to reduce turbulence of the coupled water downstream of the transducers and into the laminar flow paths.

28. The method according to claim 19 including:
positioning one of said nozzles on one side of said workpiece to discharge water coupled with ultrasonic energy onto said workpiece in a predetermined area; and
positioning another of said nozzles on the other side of the workpiece to discharge water coupled with ultrasonic energy onto said workpiece in a predetermined area opposite said area on the one side.

* * * * *